(12) United States Patent
Nakatani et al.

(10) Patent No.: US 7,776,193 B2
(45) Date of Patent: *Aug. 17, 2010

(54) CELL ELECTROPHYSIOLOGICAL SENSOR

(75) Inventors: Masaya Nakatani, Hyogo (JP); Hiroshi Ushio, Hyogo (JP); Soichiro Hiraoka, Osaka (JP)

(73) Assignee: Panasonic Corporation, Osaka (JP)

( * ) Notice: Subject to any disclaimer, the term of this patent is extended or adjusted under 35 U.S.C. 154(b) by 46 days.

This patent is subject to a terminal disclaimer.

(21) Appl. No.: 11/719,610

(22) PCT Filed: Dec. 19, 2006

(86) PCT No.: PCT/JP2006/325217

§ 371 (c)(1),
(2), (4) Date: May 17, 2007

(87) PCT Pub. No.: WO2007/072790

PCT Pub. Date: Jun. 28, 2007

(65) Prior Publication Data

US 2009/0178922 A1    Jul. 16, 2009

(30) Foreign Application Priority Data

Dec. 20, 2005  (JP)  ............................. 2005-366060
May 17, 2006  (JP)  ............................. 2006-137540

(51) Int. Cl.
*C12M 1/00* (2006.01)
*C12M 1/34* (2006.01)
*C12Q 1/00* (2006.01)
*G01N 27/00* (2006.01)

(52) U.S. Cl. ........................... 204/403.01; 204/403.03; 205/777.5; 435/287.1; 600/345; 422/98

(58) Field of Classification Search ............ 204/403.01, 204/937, 403.3, 40, 415; 205/777.5; 435/4–40.52, 435/173.4–173.6, 287.1–288.7; 600/309–367; 422/68.1–98; 436/62–71, 500–548
See application file for complete search history.

(56) References Cited

U.S. PATENT DOCUMENTS 5,183,744 A    2/1993   Kawamura et al.

(Continued)

FOREIGN PATENT DOCUMENTS

JP    02-131569 A    5/1990

(Continued)

OTHER PUBLICATIONS

Machine translation JP07-201509A, Sakukawa et al. 1995.*

(Continued)

*Primary Examiner*—Nam X Nguyen
*Assistant Examiner*—Susan Thai
(74) *Attorney, Agent, or Firm*—RatnerPrestia (57) ABSTRACT

A cell electrophysiological sensor is provided with: a well having a wall formed by at least one curved face, with opening sections being formed on the two ends thereof; a frame substrate having a through hole and an electrode; a cell electrophysiological sensor chip that is provided with a thin plate having a second through hole; and a void substrate, and in this structure, the frame substrate has a thickness greater than the thickness of the cell electrophysiological sensor chip and the opening diameter of the third opening section is made larger than the opening diameter of the fourth opening section.

22 Claims, 12 Drawing Sheets

U.S. PATENT DOCUMENTS

| | | |
|---|---|---|
| 6,315,940 B1 | 11/2001 | Nisch et al. |
| 6,682,649 B1 | 1/2004 | Petersen et al. |
| 6,984,297 B2 | 1/2006 | Nisch et al. |
| 7,006,929 B2 | 2/2006 | Oka et al. |
| 2003/0080314 A1* | 5/2003 | Nisch et al. ............... 252/62.2 |
| 2003/0113833 A1 | 6/2003 | Oka et al. |
| 2004/0011651 A1* | 1/2004 | Becker et al. ............... 204/547 |
| 2004/0033483 A1* | 2/2004 | Oka et al. ................... 435/4 |
| 2004/0152067 A1* | 8/2004 | Wang et al. ................. 435/4 |
| 2004/0197898 A1* | 10/2004 | Nakatani et al. ......... 435/287.1 |
| 2005/0112756 A1* | 5/2005 | Nakatani et al. ......... 435/287.2 |
| 2005/0221469 A1 | 10/2005 | Nakatani et al. |

FOREIGN PATENT DOCUMENTS

| | | |
|---|---|---|
| JP | 07201509 A * | 8/1995 |
| JP | 2002-508516 | 3/2002 |
| JP | 2002-518678 | 6/2002 |
| JP | WO 03/016555 A1 | 2/2003 |
| JP | 2003-511668 | 3/2003 |
| JP | 2003-511668 A | 3/2003 |
| JP | 2003-511699 | 3/2003 |
| JP | 2003-511699 A | 3/2003 |
| JP | 2003-527581 | 9/2003 |
| JP | 2004-69309 | 3/2004 |
| JP | 2004-271330 A | 9/2004 |
| JP | 2004-271331 A | 9/2004 |
| JP | 2005-156234 | 6/2005 |
| WO | WO 02/055653 | 7/2002 |
| WO | WO 02/055653 A1 | 7/2002 |
| WO | WO 03-016555 | 2/2003 |

OTHER PUBLICATIONS

Suzuki, K. et al., "The Electrophysiological Biosensor for Batch-Measurement of Cell Signals," IEEJ Trans. SM, vol. 125, No. 5, 2005, pp. 216-221.

International Search Report for corresponding PCT International Application No. PCT/JP06/325217 dated Jan. 23, 2007.

English Translation of PCT/ISA/210.

Japanese Office Action for Application No. JP 2003-392220, Jan. 26, 2010, Panasonic Corporation.

* cited by examiner

CELL ELECTROPHYSIOLOGICAL SENSOR

THIS APPLICATION IS A U.S. NATIONAL PHASE APPLICATION OF PCT INTERNATIONAL APPLICATION PCT/JP2006/325217 FILED DEC. 19, 2006.

TECHNICAL FIELD

The present invention relates to a cell electrophysiological sensor that is used for measuring cell electrophysiological phenomena, such as an intracellular electric potential or an extracellular electric potential, that is, physical and chemical changes generated by activities of a cell.

BACKGROUND ART

Conventionally, in the field of electrophysiology, a patch clamp method has been known as a method for measuring an ion channel function possessed by a cell membrane, and various functions of the ion channel have been clarified by this patch clamp method. In the cytology, there have been great concerns about the functions of the ion channel, and these are also applied to developments for medicines.

In the patch clamp method, however, since an extremely high measuring technique is required for inserting a fine micropipette into a single cell with high precision, a skilled technician is required. Therefore, when measurements with a high throughput are required, this method fails to provide an appropriate method.

For this reason, a flat-plate type probe, formed by utilizing a micromachining technique, has been developed, and this probe is suitably applied to an automated system that does not require the insertion of the micropipette to each cell individually. For example, a technique has been proposed in which: a hole is formed in a carrier that separates two areas, and by allowing electrodes placed above and below this carrier to generate an electric field, the hole is efficiently made in contact with a cell and allowed to keep this state efficiently, and electrical measurements are carried out between the upper and lower electrodes so that electrophysiological measurements can be carried out on the cell (see Patent Document 1). Moreover, another technique has been proposed in which; a plurality of through holes are formed in a flat-plate device, and a continuous layer of a cell adhered to these is used for measuring potential-dependent ion channel activities by using electrodes (see Patent Document 2).

Moreover, still another technique has been proposed in which: microelements respectively attached to the inside of each of a plurality of cavities formed on a substrate are prepared, and by pressure-reducing passages connected to these microelements, a cell is attracted to the microelements so that electrophysiological phenomena of the cell are measured (see Patent Document 3). Still another technique has been proposed in which: holes are formed in a flat portion of a substrate, and a reference electrode and a measuring electrode are integrally formed in the substrate so that electrophysiological phenomena of a cell are measured (see Patent Document 4). Furthermore, still another method has been proposed in which: on a surface through which one channel penetrates, a cell is positioned by a suction process applied from the lower surface of the cell, and one portion of the lower surface of the cell is ruptured by increasing a pressure difference so that the cell contained in a liquid is measured (see Patent Document 5).

Another apparatus has been proposed in which: an orifice is sealed by an object in use, and first and second cavity portions, electrically insulated by this object, are formed so that electrical measurements are carried out on the object in a medium based upon changes in impedance between the electrodes respectively placed on the first and second cavity portions (see Patent Document 6).

Still another technique has been proposed in which an extracellular potential measuring device, which has a well that has a cell holding means and is formed on a substrate, a measuring electrode used for detecting an electric signal of the well and a reference electrode, is used for measuring the extracellular electrical potential (see Patent Document 7).

Moreover, still another apparatus has been proposed in which: an orifice is sealed by an object, and by measuring an electrode impedance between cavities electrically insulated by the object, a change in the state of the object can be detected, and a liquid supplying means, provided with a liquid supplying capillary tube and a liquid suction capillary tube used for quickly removing or exchanging the liquid environment in which the object is placed, has also been proposed (see Patent Document 6).

In addition to these, a device in which through holes having a diameter of several μms are formed on a flat plate made from $SiO_2$ has been known. These through holes have the same function as that of a tip hole that is formed in the glass pipette used in the patch clamp method. By conducting a suction process or the like on a cell from the back surface side of the flat plate, the cell can be automatically attracted to the through hole to adhere thereto; thus, it becomes possible to easily measure the extracellular electric potential.

However, the main objective of the above-mentioned conventional cell electrophysiological sensor is to easily measure electrophysiological phenomena of a cell, without the necessity of using a microprobe to be used in the conventional patch clamp method. In particular, the liquid supplying means, disclosed in Patent Document 6, is an effective means used for quickly removing or exchanging the liquid environment on the periphery of a cell. However, although it is very important to place an extremely thin pipe serving as the liquid supplying means on the periphery of a cell with high precision, to insert the pipe in the liquid with high precision is very difficult since in the liquid, the influence of a surface tension exerted onto the pipe is not negligible. Moreover, when, upon supplying a liquid on the periphery of a cell, a direct flow is generated toward the cell, the flow tends to be unstable in the case when the flow is made too strong so as to quickly supply the liquid.

Patent Document 1: Japanese Translation of PCT Publication No. 2002-508516

Patent Document 2: Japanese Translation of PCT Publication No. 2002-518678

Patent Document 3: U.S. Pat. No. 6,315,940

Patent Document 4: Japanese Translation of PCT Publication No. 2003-511668

Patent Document 5: Japanese Translation of PCT Publication No. 2003-511699

Patent Document 6: Japanese Translation of PCT Publication No. 2003-527581

Patent Document 7: International Publication WO02055653

DISCLOSURE OF THE INVENTION

A cell electrophysiological sensor in accordance with the present invention is provided with: a well having a first wall formed by at least one curved face, with a first opening section and a second opening section being formed on the two ends of the first wall; a frame substrate having a first through hole with a third opening section that is made in contact with the second opening section and a fourth opening section; a cell electrophysiological sensor chip that has a thin plate having at least one second through hole, and is embedded in the first through hole; and a void substrate having a void so as to make contact with the fourth opening, and in this structure, the thin plate of the cell electrophysiological sensor chip is placed below the end portion of the third opening section.

With this arrangement, upon application, by allowing medicine and other liquids to be positively supplied and sucked to the periphery of a cell that is placed at a specific position in a liquid, measurements can be efficiently carried out on cell electrophysiological phenomena.

REFERENCE MARKS 1, 1A, 1B, 1C Well
2 Frame substrate
3 Void substrate
4 Cell electrophysiological sensor chip
5 First through hole
6 First opening section
7 Second opening section
9 Third opening section
10 Fourth opening section
11 Passage
12 Groove
13 First wall
14 Second wall
15 Void
16 Second through hole
17 Thin plate
18 Micropipette
19 Cell
20 Groove
21 Concave section
22 Convex portion
23 First electrode
24 Second electrode
25 Third electrode
26 Extracellular fluid
27 Intracellular fluid
28 Sealing agent
30 Wiring electrode
31 Void structured body

PREFERRED EMBODIMENTS FOR CARRYING OUT OF THE INVENTION

With reference to attached drawings, the following description will discuss a cell electrophysiological sensor in accordance with one embodiment of the present invention.

Embodiment 1

Figure 1:
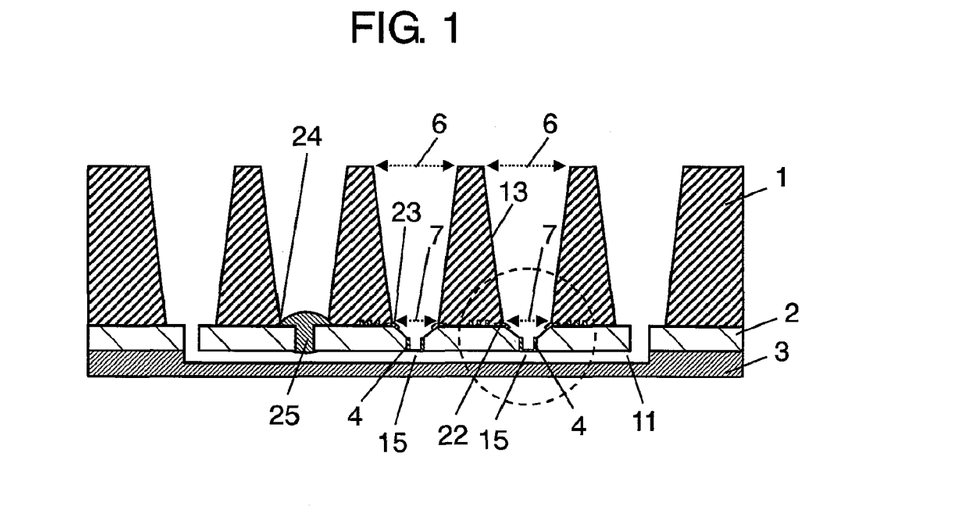
FIG. 1 is a cross-sectional view showing a cell electrophysiological sensor in accordance with embodiment 1 of the present invention.
Figure 2:
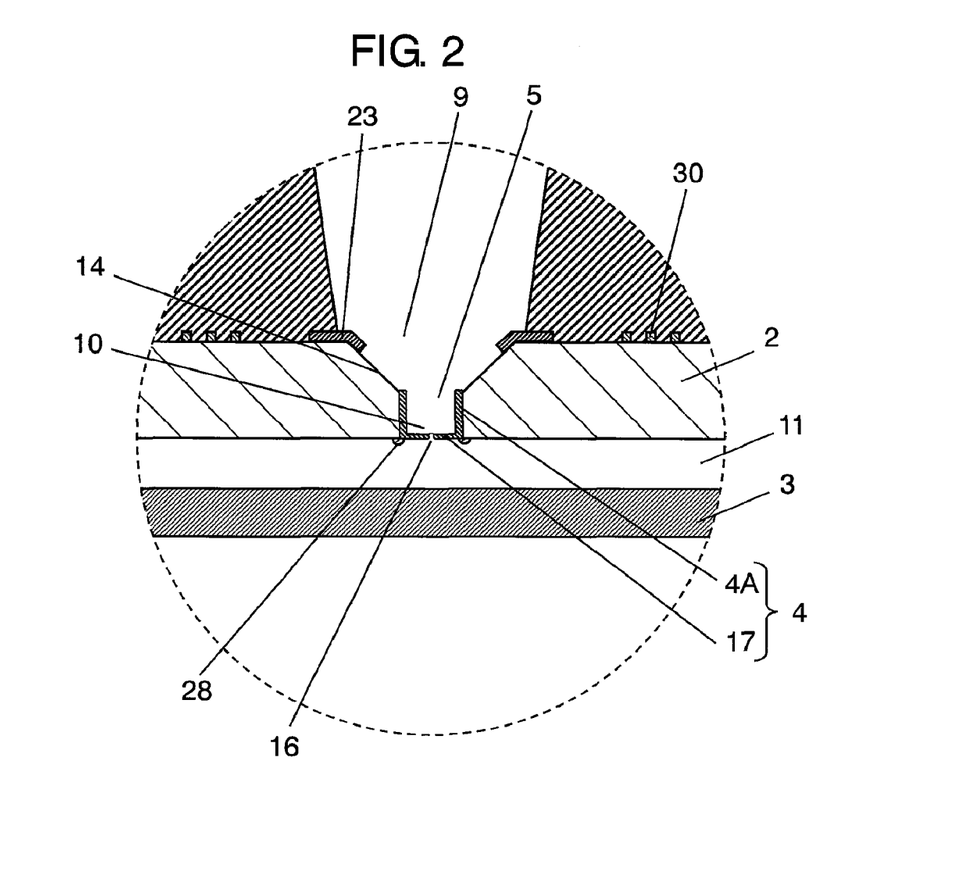
FIG. 2 is an enlarged cross-sectional view that shows an essential portion of the cell electrophysiological sensor in accordance with embodiment 1 of the present invention.
Figure 3:
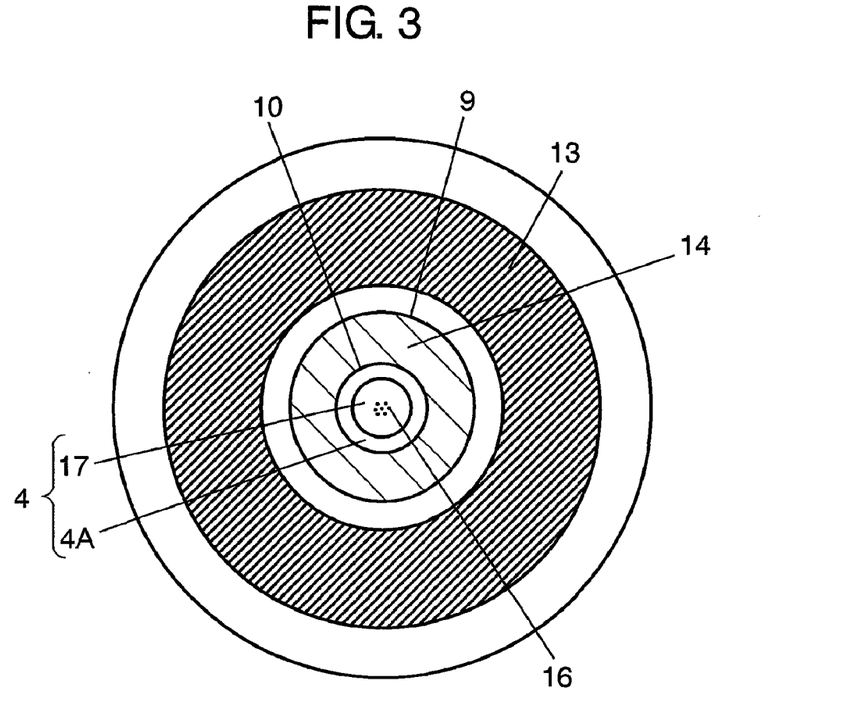
FIG. 3 is an enlarged top view that shows an essential portion of the cell electrophysiological sensor in accordance with embodiment 1 of the present invention.

FIG. 1 is a cross-sectional view showing a cell electrophysiological sensor in accordance with embodiment 1 of the present invention, FIG. 2 is an enlarged cross-sectional view showing an essential portion of FIG. 1, and FIG. 3 is an enlarged top view showing the essential portion. As shown in FIGS. 1 to 3, well 1, made from resin, is provided with first wall 13 formed by at least one curved face, and first opening section 6 and second opening section 7 that are formed on the two ends thereof. As indicated by arrows in FIG. 1, first opening section 6 corresponds to an opening portion that is formed on the upper portion of well 1. In the same manner, second opening section 7 corresponds to an opening portion that is formed on the lower portion of well 1, as indicated by arrows in FIG. 1. Here, as shown in FIG. 3, first opening section 6 and second opening section 7 are formed in substantially round opening portions. In the present embodiment, first opening section 6 and second opening section 7 are formed as the substantially round opening portions; however, not limited to round shapes, each of these may be formed in substantially an elliptical shape or a rectangular shape. Moreover, in first wall 13 of well 1, the opening diameter of first opening section 6 is made greater than the opening diameter of second opening section 7, with first wall 13 thereof being formed in a tapered shape.

Frame substrate 2, made from resin, is made in contact with second opening section 7. First through hole 5 having third opening section 9 and fourth opening section 10 on its two ends is formed in frame substrate 2. Third opening section 9 corresponds to an opening portion that is formed on the upper face of frame substrate 2. In the same manner, fourth opening section 10 corresponds to an opening portion that is formed on the lower face of frame substrate 2. Here, first through hole 5 has a tapered shape, with the opening diameter of third opening section 9 being made larger than that of fourth opening section 10, that is, a cone shape as shown in FIG. 2.

Moreover, void substrate 3, made from resin, is made in contact with fourth opening section 10, and void substrate 3 is provided with voids 15 formed on a lower portion of fourth opening section 10. Respective voids 15 are mutually connected to each other, and utilized as passage 11 for medicine or the like.

Moreover, cell electrophysiological sensor chip 4 having holding portion 4A (side wall portion) and thin plate 17 is embedded in first through hole 5 of frame substrate 2, and sealed by sealing agent 28. Thin plate 17 is provided with at least one second through hole 16. Here, second through hole 16 is a through hole having such a fine diameter that it is not illustrated in FIG. 2. The thickness of frame substrate 2 is made greater than the thickness of cell electrophysiological sensor chip 4. In this case, thin plate 17 of sensor chip 4 is positioned below third opening section 9 that is the opening portion on the upper side of first through hole 5. Moreover, as shown in FIG. 2, first through hole 5 is designed so that third opening section 9 is gradually narrowed. First through hole 5 forms a hole perpendicular to frame substrate 2 at a position where it is made to have substantially the same size as the outer shape of cell electrophysiological sensor chip 4, and is allowed to communicate with fourth opening section 10. In other words, the cell electrophysiological sensor of embodiment 1 has taper-shaped second wall 14 in which the size of third opening section 9 is set not larger than the size of second opening section 7, and is made also gradually smaller so as to substantially match the size of the top face of cell electrophysiological sensor chip 4. With this arrangement, as will be described later in the explanation of the operation, upon charging cells, medicine, culture solution, extracellular fluid and the like into well 1, it is possible to allow these to positively reach the vicinity of thin plate 17 of cell electrophysiological sensor chip 4 on which second through hole 16 is formed. Therefore, it becomes possible to achieve a cell electrophysiological sensor that enables an effective measuring process.

All well 1, frame substrate 2 and void substrate 3 are made of resin, and with respect to the resin, a thermoplastic resin is preferably used. With this arrangement, these members can be firmly joined to one another by means of thermal fusion or the like, without the necessity of, particularly, using a bonding agent. Moreover, well 1, frame substrate 2 and void substrate 3 are preferably made from a thermoplastic resin containing at least one of polycarbonate resin, polyethylene resin, olefin polymer resin and polymethacrylic acid methylacetate resin. These materials are easily joined, in particular, through thermal fusion. Moreover, well 1, frame substrate 2 and void substrate 3 are also preferably made from at least one material selected from the group consisting of a cyclic olefin polymer, a linear olefin polymer, a cyclic olefin copolymer made by copolymerizing these, and polyethylene. In particular, the cyclic olefin copolymer is superior in transparency and in resistance against alkaline or acidic inorganic medicines, and best suited for manufacturing processes or the application environment of the present invention.

Here, FIG. 1 shows a structure in which a plurality of cell electrophysiological sensor chips 4 are formed; however, the scope of the present invention is not intended to be limited by this structure. Moreover, FIG. 1 also shows a state in which first electrode 23, second electrode 24 and third electrode 25 are installed on frame substrate 2. These electrodes are used for measuring electric indexes generated in the sensor unit, such as an electric potential and a current; however, the scope of the present invention is not intended to be limited by the shape, material and the like of these. Moreover, these electrodes may be preliminarily formed as an integral part with the cell electrophysiological sensor, or may be designed so as to be inserted into the cell electrophysiological sensor upon measurement.

Here, wiring electrodes 30 have an electrode pattern in which a plurality of cell electrophysiological sensor chips 4 are arranged in a matrix form.

The following description will discuss a method used for measuring electrophysiological activities of a cell by using the cell electrophysiological sensor of the present invention. FIGS. 4 to 11 are cross-sectional views that explain the measuring method in which the cell electrophysiological sensor of the present invention is used.

Figure 4:
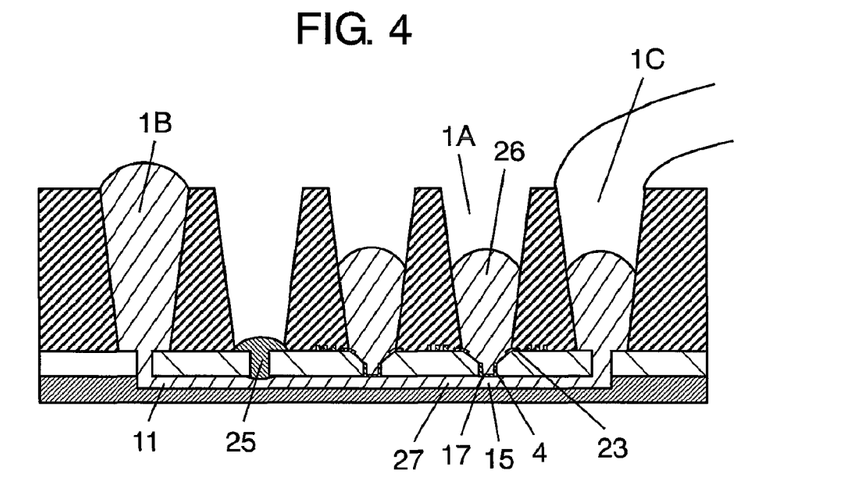
FIG. 4 is a cross-sectional view that explains a measuring method for the cell electrophysiological sensor in accordance with embodiment 1 of the present invention.

First, as shown in FIG. 4, intracellular fluid 27 is sucked from well 1B to well 1C, and injected into void 15, while extracellular fluid 26 is injected into well 1A. Here, in the case of mammal muscle cells, intracellular fluid 27 is typically represented by an electrolyte to which 155 mM of $K^+$ ions, about 12 mM of $Na^+$ ions and about 4.2 mM of $Cl^-$ ions are added, and extracellular fluid 26 is represented by an electrolyte to which about 4 mM of $K^+$ ions, about 145 mM of $Na^+$ ions and about 123 mM of $Cl^-$ ions are added. In this state, between first electrode 23 installed in well 1 and third electrode 25 made of silver chloride or the like installed in void 15, a resistance value in a range from 100 kΩ to 10 MΩ can be measured. Third electrode 25 seals the upper and lower portions of frame substrate 2 so that intracellular fluid 27 inside passage 11 is prevented from leaking toward the well side, and also serves as an electrode for use in reference. In other words, intracellular fluid 27 or extracellular fluid 26, which is an electrolyte, is allowed to permeate through second through hole 16 formed inside thin plate 17 of cell electrophysiological sensor chip 4 so that an electric circuit is formed between first electrode 23 and third electrode 25.

Figure 5:
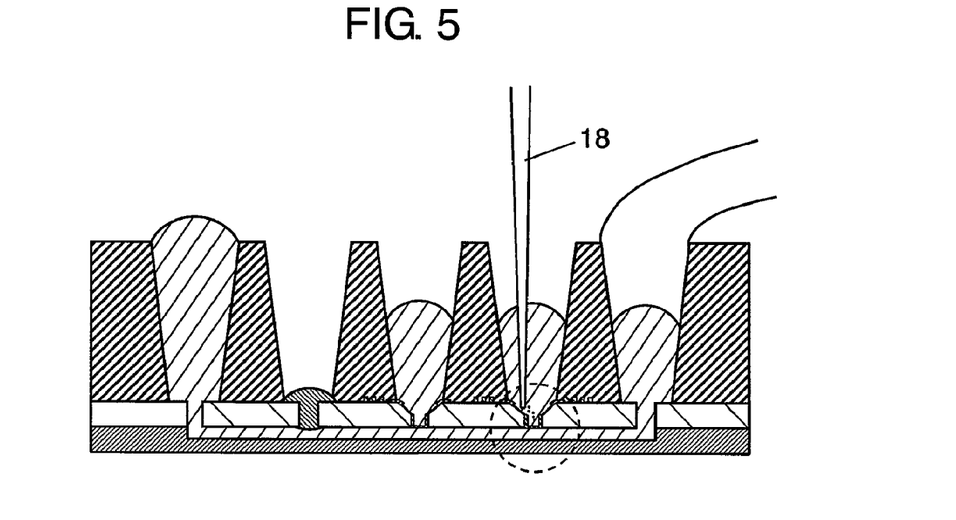
FIG. 5 is a cross-sectional view showing a cell electrophysiological sensor in accordance with embodiment 1 of the present invention.
Figure 6:
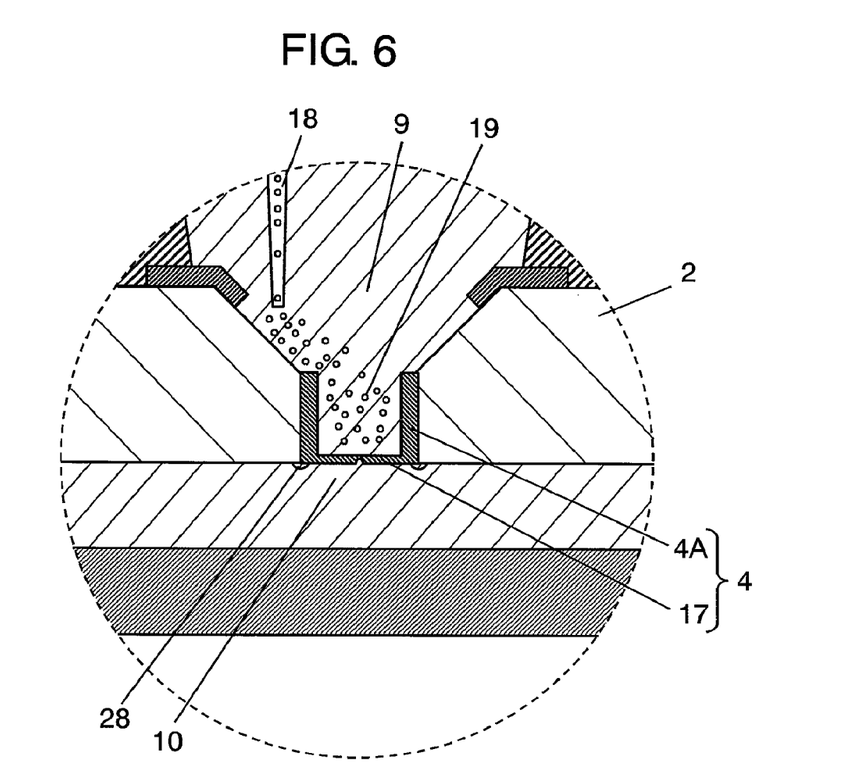
FIG. 6 is an enlarged cross-sectional view that shows an essential portion of the cell electrophysiological sensor in accordance with embodiment 1 of the present invention.

Next, as shown in FIGS. 5 and 6, cells 19 are charged by using micropipette 18. Here, FIG. 6 is an enlarged cross-sectional view that shows an essential portion of the cell electrophysiological sensor in accordance with embodiment 1 of the present invention, and represents a round portion surrounded by a broken line shown in FIG. 5. As shown in FIG. 6, the opening diameter of third opening section 9 is made larger than that of fourth opening section 10, with first through hole 5 having a tapered shape being formed on frame substrate 2. Therefore, a structure which allows cells 19 thus charged to easily reach the vicinity of thin plate 17 of cell electrophysiological sensor chip 4 is achieved.

Figure 7:
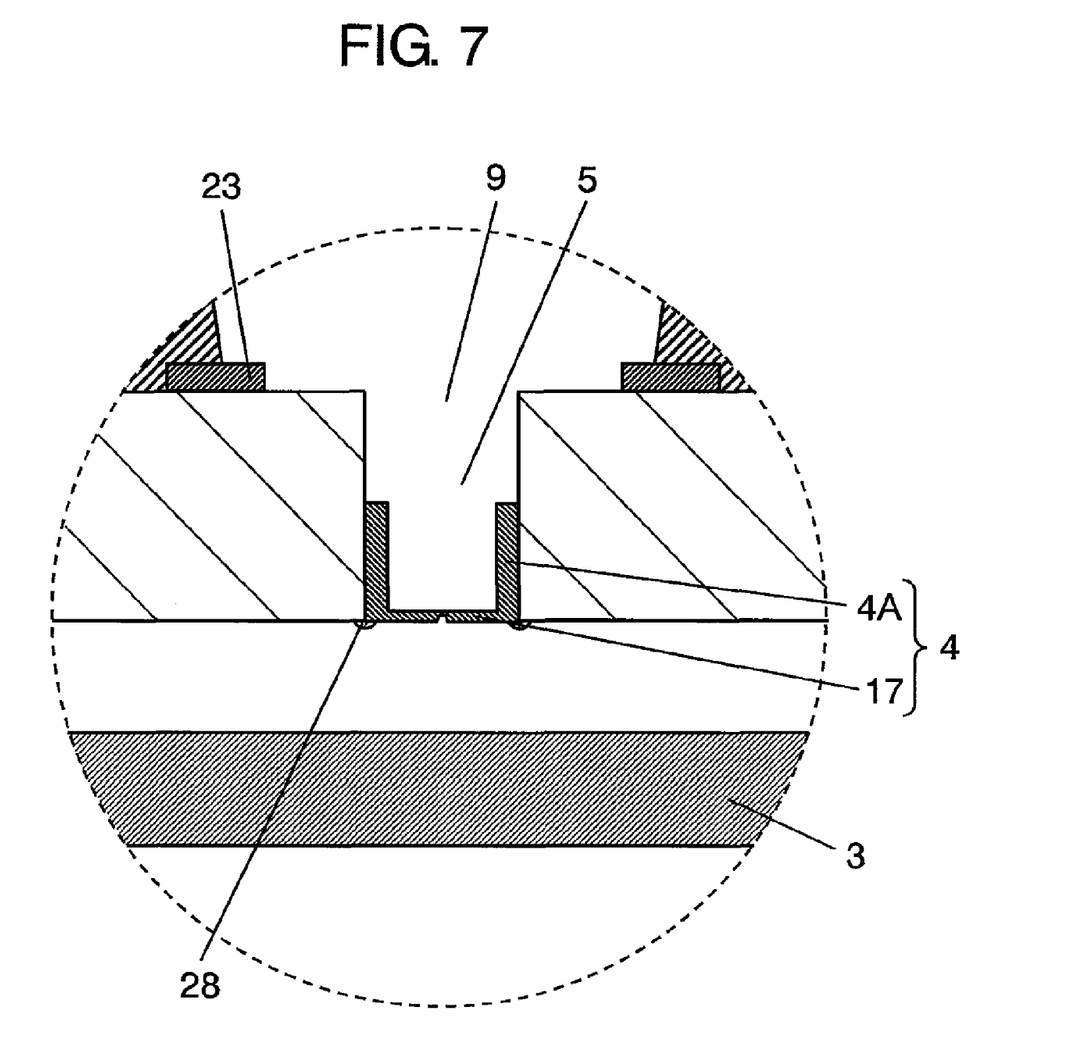
FIG. 7 is an enlarged cross-sectional view that shows an essential portion of the cell electrophysiological sensor in accordance with embodiment 1 of the present invention.
Figure 8:
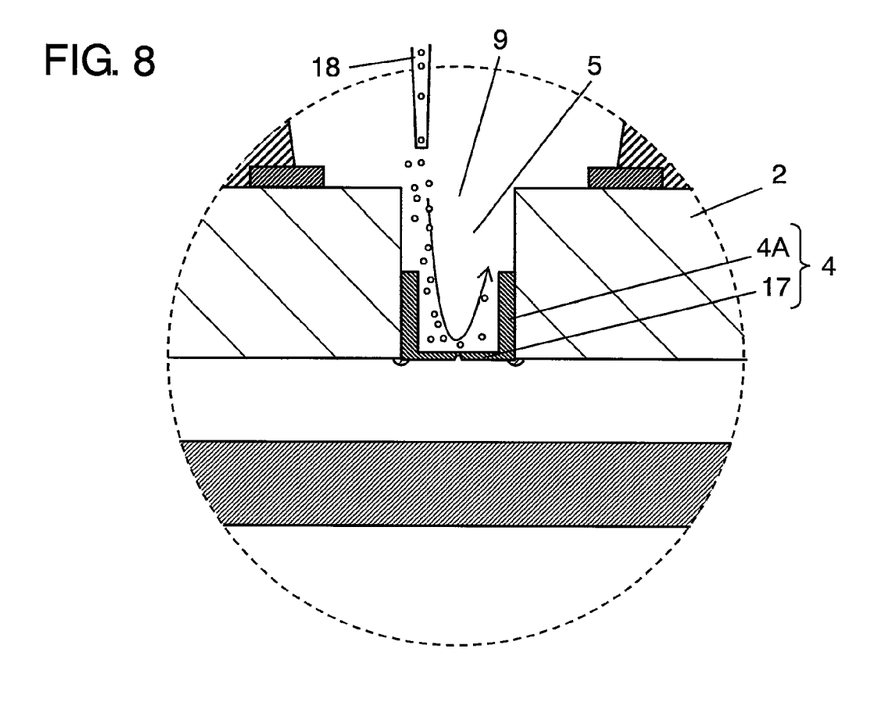
FIG. 8 is a cross-sectional view showing a cell electrophysiological sensor in accordance with embodiment 1 of the present invention.

Here, as shown in FIG. 7, the shape of first through hole 5 of frame substrate 2 may be formed in a perpendicular hole; however, this structure presumably makes it difficult for cells, medicines, culture solution, extracellular fluid and the like to reach the vicinity of thin plate 17 when charged therein, in comparison with the above-mentioned tapered shape. Therefore, the solution is preferably charged, with the position of micropipette 18 to be inserted from above upon charging these being shifted slightly from the center of first through hole 5, preferably, horizontally with a distance of about 100 to 500 μm, as shown in FIG. 8. With this arrangement, the flow of the solution is generated inside first through hole 5 so that the solution is allowed to positively reach the vicinity of thin plate 17.

In accordance with the present embodiment, since thin plate 17 is positioned below third opening section 9 that is the opening on the upper side of first through hole 5; therefore, upon charging cells, medicines and the like from above, the resulting solution forms not a direct flow toward the vicinity of thin plate 17, but a flow along the wall face of first through hole 5. Thus, a more moderate flow is generated.

Figure 9:
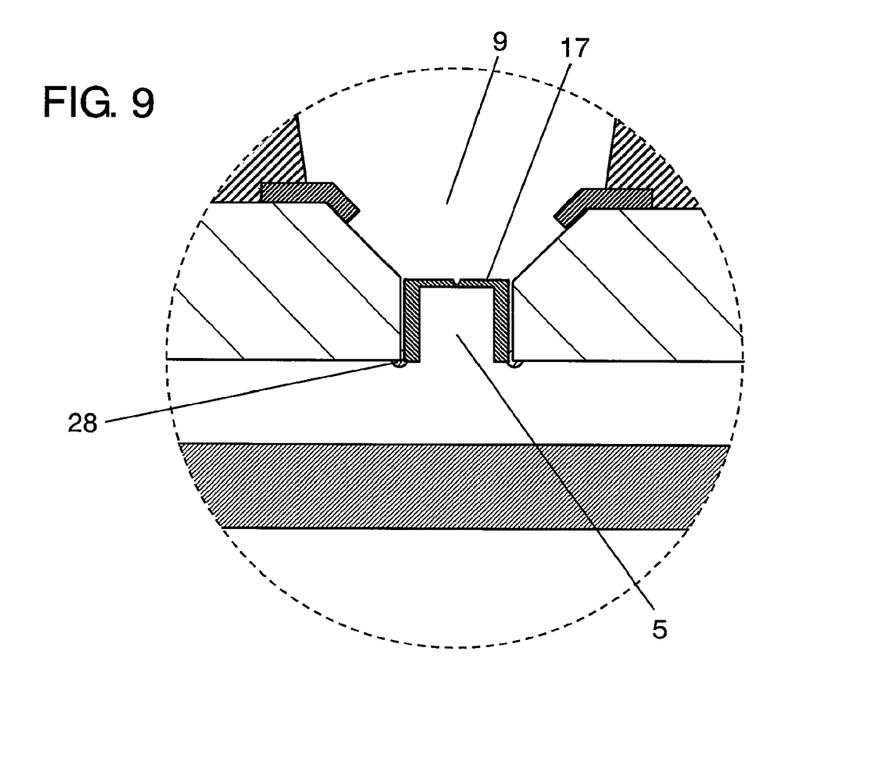
FIG. 9 is a cross-sectional view showing a cell electrophysiological sensor having another structure in accordance with embodiment 1 of the present invention.
Figure 10:
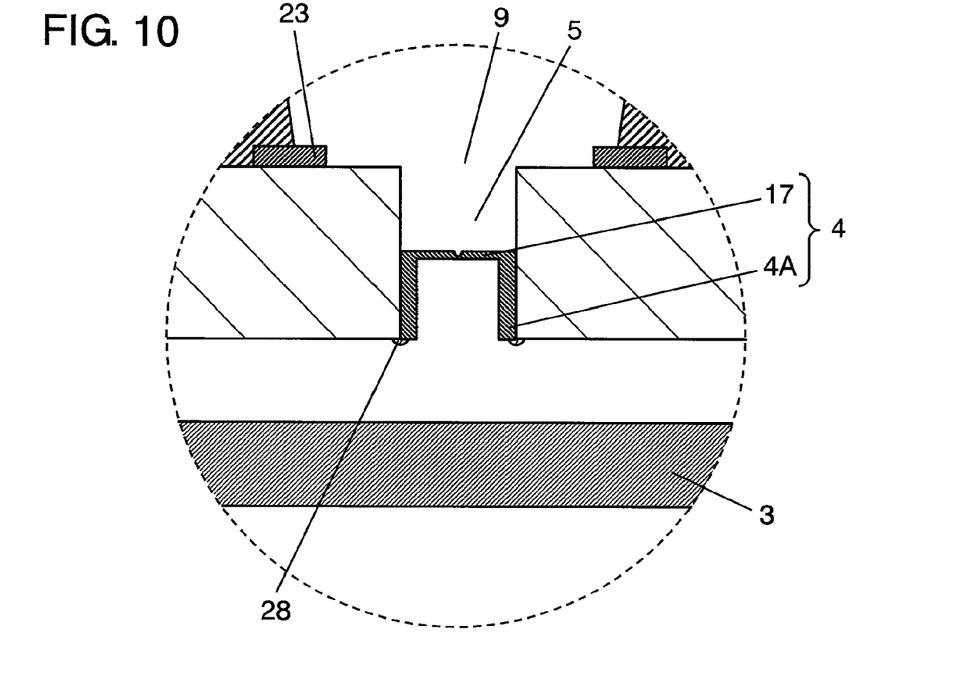
FIG. 10 is a cross-sectional view showing a cell electrophysiological sensor having still another structure in accordance with embodiment 1 of the present invention.

Cell electrophysiological sensor chip 4 of the present invention has a shape in which thin plate 17 is held on supporting portion 4A. The reason that cell electrophysiological sensor chip 4 is formed, with thin plate 17 being held by holding portion 4A, is because, since the thickness of thin plate 17 is as thin as 100 μm or less, it is difficult to handle this as a single part. Moreover, as shown in FIGS. 9 and 10, upon placing cell electrophysiological sensor chip 4 on first through hole 5, thin film 17 may be placed closer to third opening section 9. This selection should be made optimally depending on what conditions (flow rate, flow direction, or the like) are used to generate a flow of the cells, medicines and the like to be charged, or depending on the characteristics (for example, floating property, viscosity, size, density, or the like) of cells 19 to be measured. For example, in the case of a low density of the cell, when a step difference between thin plate 17 and third opening section 9 is made larger, with thin plate 17 being placed lower, the flow resistance of the extracellular fluid becomes greater in vicinity of thin plate 17. Therefore, the flow of the extracellular fluid becomes moderate so that the trapping rate of cells is increased. In contrast, in the case of a high density of the cell, when thin plate 17 is made closer to third opening section 9 with thin plate 17 being placed higher, the flow of the extracellular fluid becomes faster. Therefore, the cells can be trapped more quickly.

Figure 11:
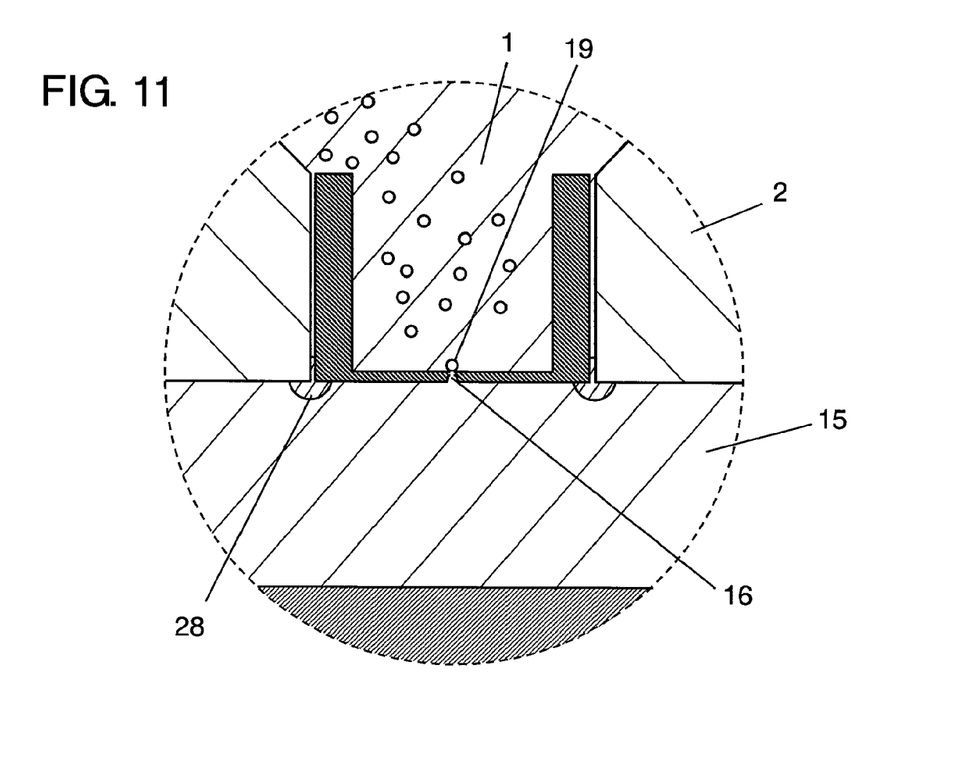
FIG. 11 is an enlarged cross-sectional view that shows an essential portion of the cell electrophysiological sensor in accordance with embodiment 1 of the present invention.

Next, when intracellular fluid 27, filled in void 15, is sucked as shown in FIG. 11, cells 19 are attracted toward second through hole 16 consequently to plug second through hole 16, with the result that the electric resistance between well 1 and void 15 becomes sufficiently high. In this state, when an electric potential inside or outside of cell 19 is varied due to electrophysiological activity of cell 19, it is possible to achieve a measurement with high precision, even in the case of a slight potential difference or current.

Figure 12:
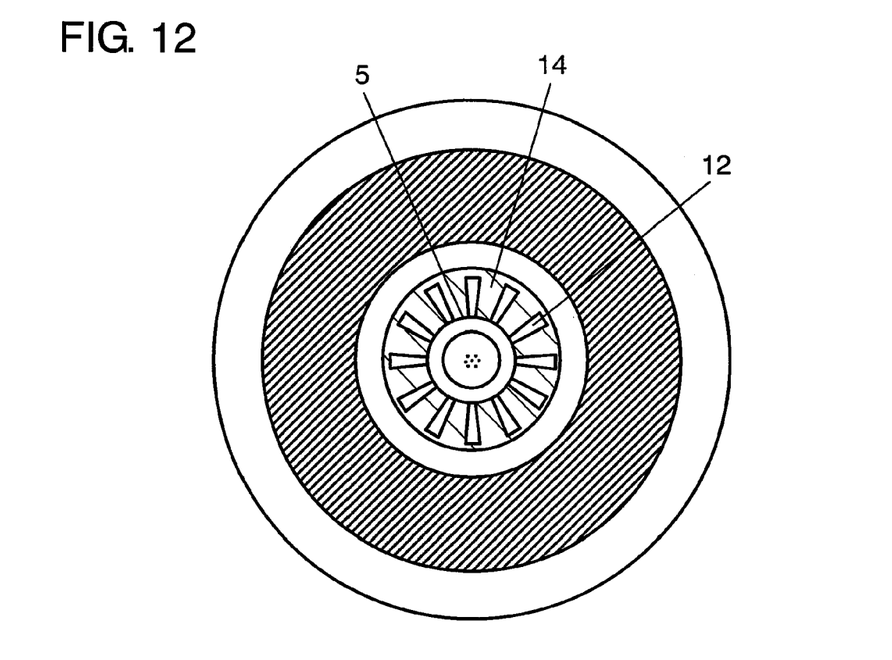
FIG. 12 is a top view showing a cell electrophysiological sensor having still another structure in accordance with embodiment 1 of the present invention.
Figure 13:
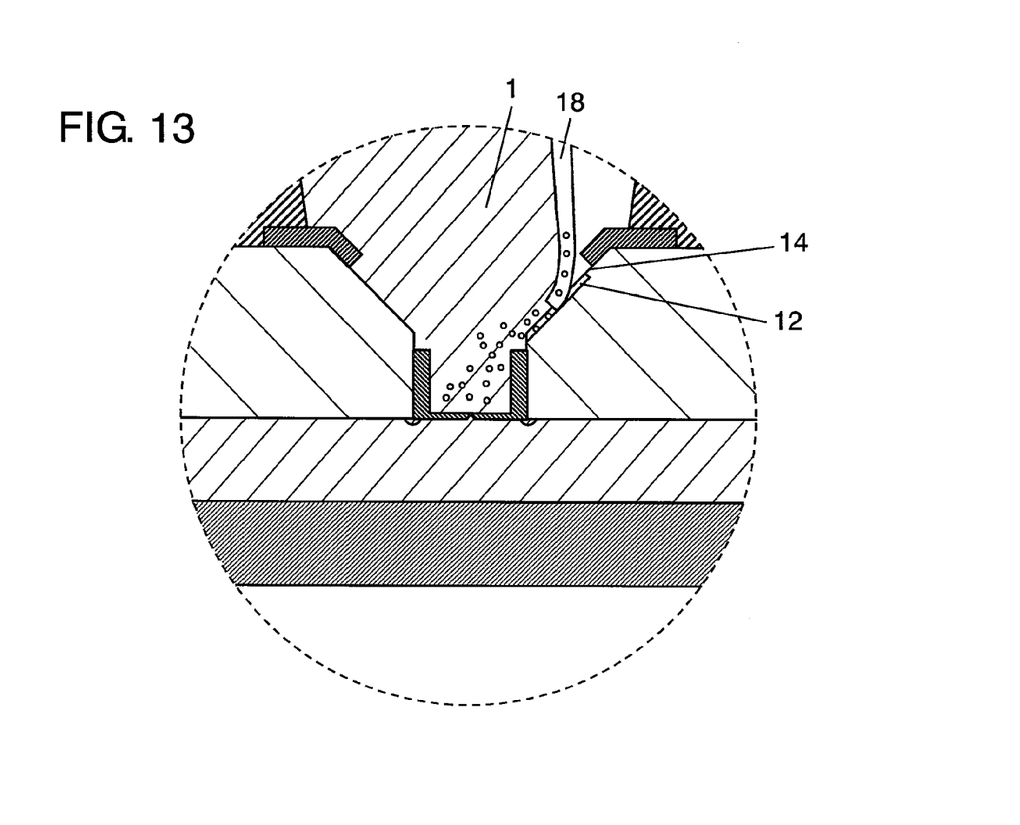
FIG. 13 is an enlarged cross-sectional view that shows an essential portion of the cell electrophysiological sensor in accordance with embodiment 1 of the present invention.

Moreover, in another example of the present embodiment 1, at least one groove 12 is formed radially toward first through hole 5 in second wall 14 that is connected to third opening section 9 of frame substrate 2 as shown in FIG. 12. Groove 12 is preferably formed in a linear shape. With this shape, even in the case when, upon insertion of micropipette 18 from well 1, micropipette 18 is subjected to a stress by the surface tension and the like of the solution in well 1 to cause difficulty in carrying out a positioning process with high precision, groove 12 formed on second wall 14 serves as a guide, and directs tip of micropipette 18 toward a desired direction so that cells 19, medicines and the like can be more positively charged to the vicinity of cell electrophysiological sensor chip 4.

Figure 14:
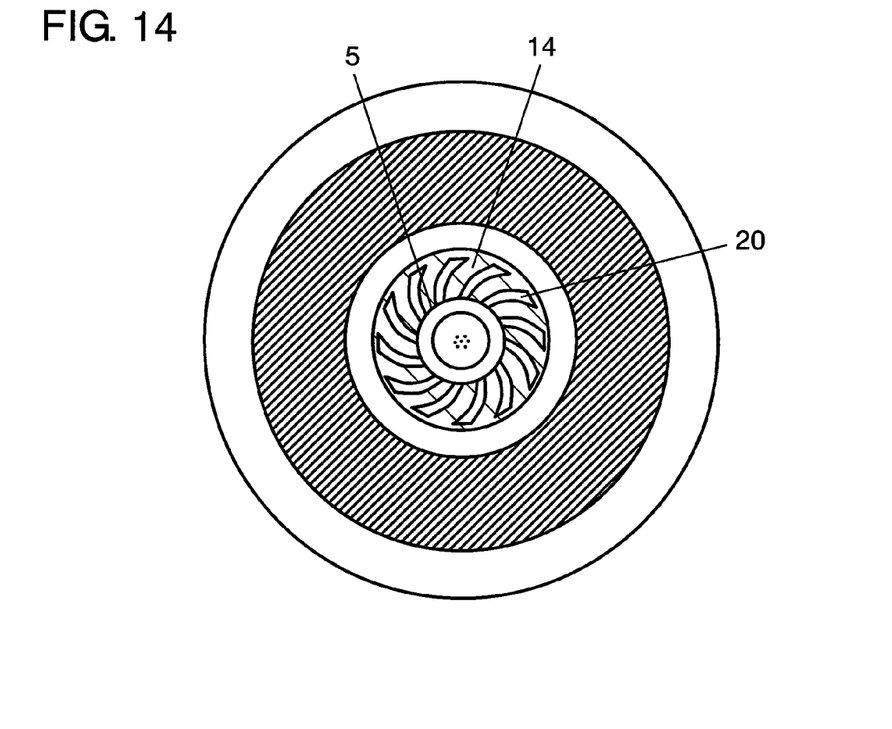
FIG. 14 is a top view showing a cell electrophysiological sensor having still another structure in accordance with embodiment 1 of the present invention.

In still another example of the present embodiment 1, at least one groove 20 may be formed in a helical shape on second wall 14 of frame substrate 2 toward the center of first through hole 5, as shown in FIG. 14. By forming such helical groove 20 on second wall 14, the liquid to be charged by micropipette 18 is allowed to flow along helical groove 20 so that the mixing process of medicines in the container of well 1 can be easily carried out.

Figure 15:
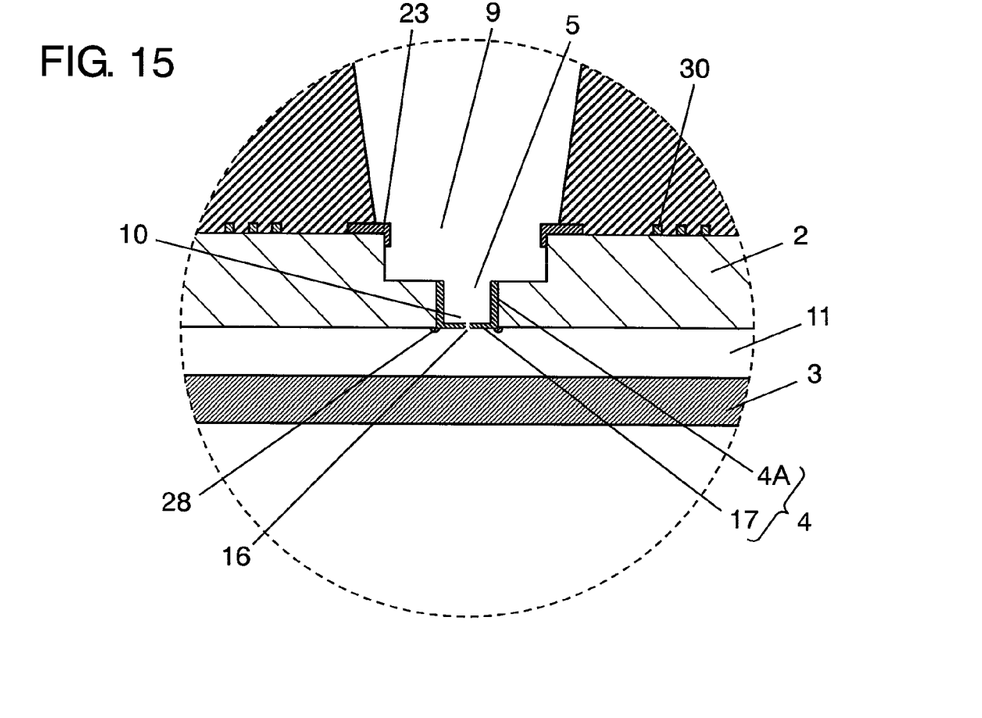
FIG. 15 is a cross-sectional view showing a cell electrophysiological sensor having still another structure in accordance with embodiment 1 of the present invention.
Figure 16A:
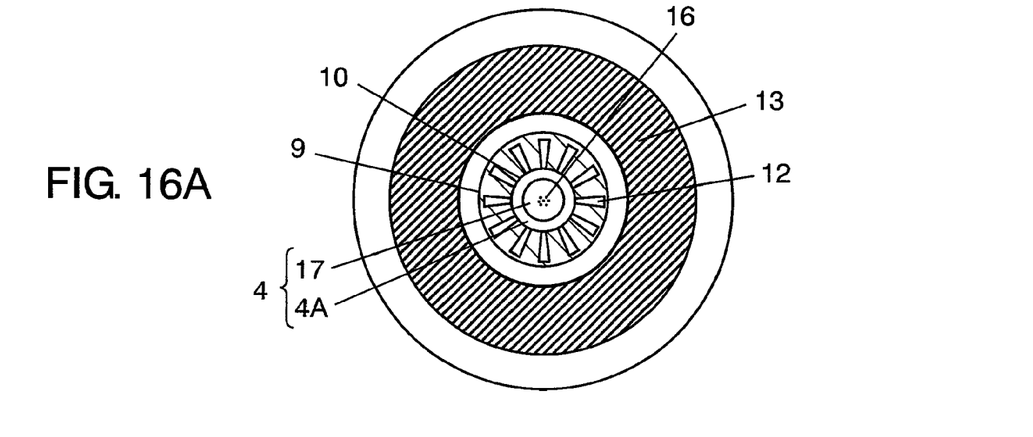
FIG. 16A is a top view showing a cell electrophysiological sensor having still another structure in accordance with embodiment 1 of the present invention.

Moreover, in another structure of the present embodiment 1, as shown in FIG. 15, the size of third opening section 9 of first through hole 5 may be set not larger than the size of second opening section 7, and may also be set greater than the size of fourth opening section 10, and the inner wall on third opening section 9 side may be formed so as to be perpendicular to fourth opening section 10 so that first through hole 5 is formed in a so-called counter bore shape. In other words, a counter bore is formed so as to have substantially the same size up to the height of the upper face of cell electrophysiological sensor chip 4, and the bottom face, which forms a plane, is formed on the same face as the upper face of cell electrophysiological sensor chip 4. The formation of such a counter bore shape is more advantageous in that the machining process is more easily carried out in comparison with the aforementioned tapered shape. Here, cell electrophysiological sensor chip 4, which is embedded in first through hole 5 of the frame substrate, has a thickness smaller than the thickness of frame substrate 2. Moreover, as shown in FIG. 16A, at least one groove 12 may be formed toward the center of first through hole 5 on the bottom face of third opening section 9 formed as the counter bore. Here, FIG. 16A shows a structure which is provided with twelve grooves 12; however, the present invention is not intended to be limited by this number. By using this groove 12, it becomes possible to stabilize the flow of a liquid located in the vicinity of the bottom face having the counter bore shape.

Figure 16B:
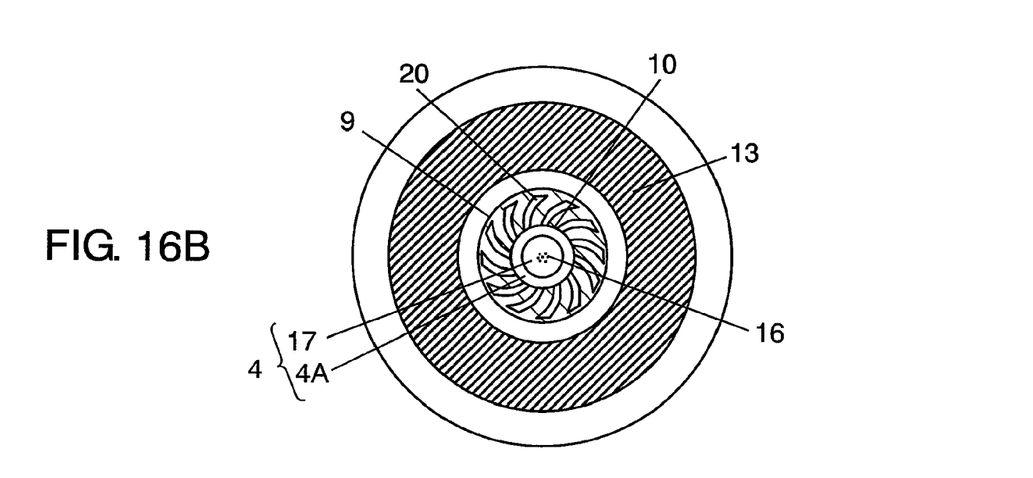
FIG. 16B is a top view showing a cell electrophysiological sensor having still another structure in accordance with embodiment 1 of the present invention.

Moreover, as shown in FIG. 16B, at least one groove 20 having a helical shape may be formed on the bottom face of third opening section 9 formed as the counter bore toward the center of first through hole 5. With this structure, when a liquid enters the inside of first through hole 5, the flow of the liquid is generated so as to form a helical shape by helical groove 20. Therefore, this structure is advantageous in that the mixing process of different liquids can be carried out smoothly. FIG. 16B shows a structure which is provided with twelve grooves 20; however, the present invention is not intended to be limited by this number.

Figure 16C:
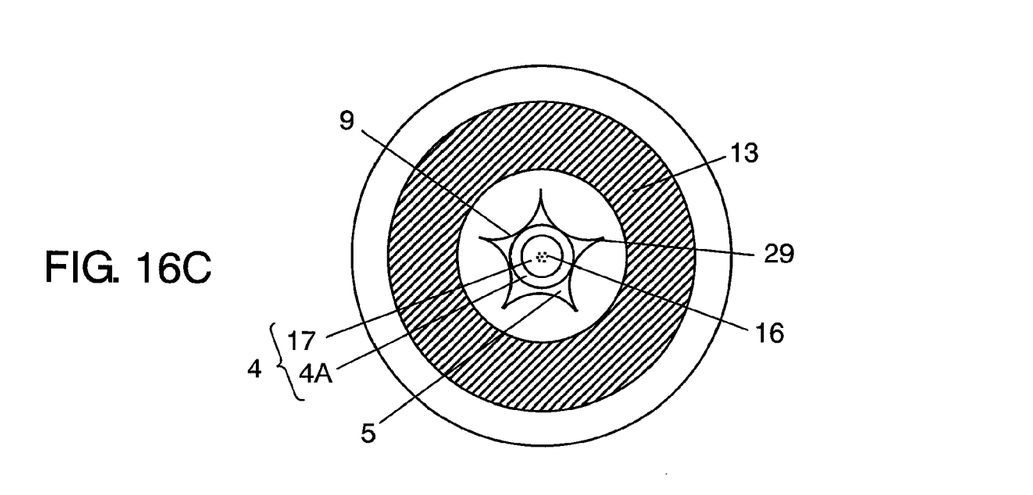
FIG. 16C is a top view showing a cell electrophysiological sensor having still another structure in accordance with embodiment 1 of the present invention.

Moreover, as shown in FIG. 16C, concave section 29 having a star shape with a plurality of acute apexes may be formed on the bottom face of third opening section 9 of first through hole 5. This structure makes the acute apex portions of the concave section hardly get wet by the liquid. Consequently, when the liquid enters the inside of first through hole 5, bubbles are concentrated on center of concave section 29, and then transmitted to third opening section 9 side so that the bubbles are easily removed. With this arrangement, when the liquid enters the inside of first through hole 5, it is possible to lower the passage resistance, and consequently to positively transfer the liquid. FIG. 16C shows a structure in which star-shaped concave section 29 has five acute apexes; however, the present invention is not intended to be limited by this number.

Figure 17:
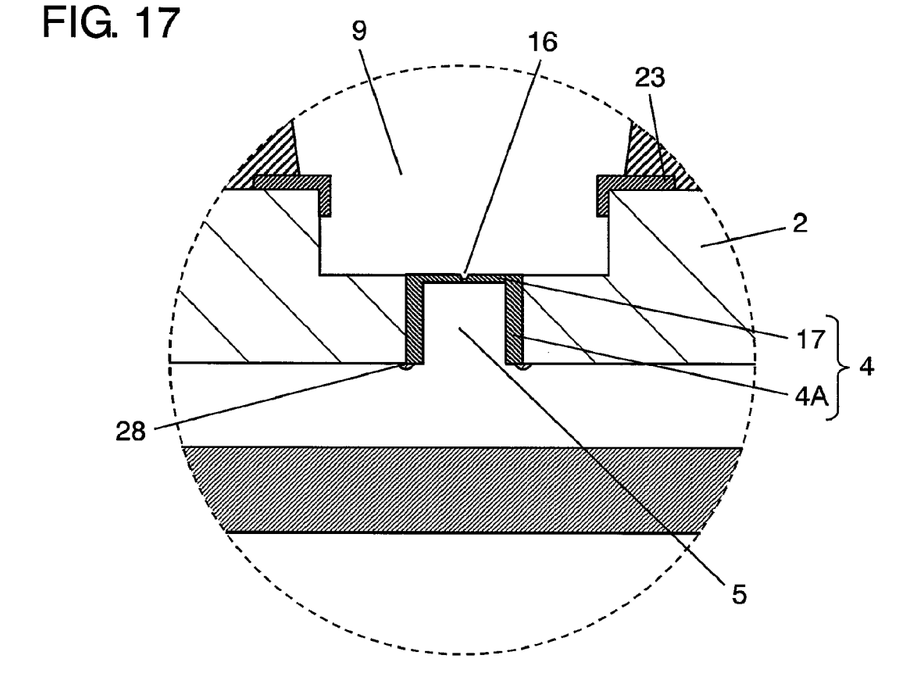
FIG. 17 is a cross-sectional view showing a cell electrophysiological sensor having still another structure in accordance with embodiment 1 of the present invention.

Additionally, when cell electrophysiological sensor chip 4 having a so-called counter bore shape in which the inner wall face on third opening section 9 side is made perpendicular to fourth opening section 10 as described earlier is placed on first through hole 5, thin plate 17 may be made to come closer to third opening section 9 side as shown in FIG. 17. This selection is made on demand depending on the characteristics (for example, floating property, adsorption, size, mass, etc.) of the cell to be measured.

Embodiment 2

With reference to Figures, the following description will discuss a cell electrophysiological sensor in accordance with embodiment 2 of the present invention. Here, in the Figures, those constituent members having the same functions as those of embodiment 1 are indicated by the same reference marks.

Figure 18:
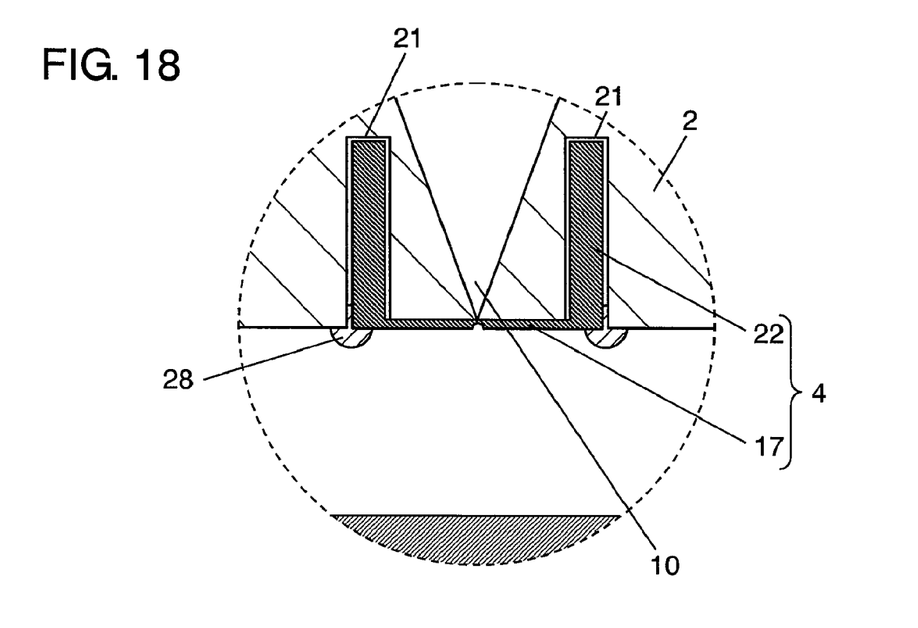
FIG. 18 is an enlarged cross-sectional view that shows a chip portion of a cell electrophysiological sensor in accordance with embodiment 2 of the present invention.

FIG. 18 is an enlarged cross-sectional view showing a chip portion of a cell electrophysiological sensor in accordance with the present embodiment 2. Although it has the same structure as embodiment 1 in that it is configured by well 1, frame substrate 2, void substrate 3 and cell electrophysiological sensor chip 4, this sensor is particularly different in the shapes of frame substrate 2 and cell electrophysiological sensor chip 4.

In other words, as shown in FIG. 18, frame substrate 2 is designed so that third opening section 9 is made larger than fourth opening section 10, and concave section 21 is formed along the peripheral edge portion of fourth opening section 10. In contrast, convex portion 22 is formed along the periphery of thin plate 17 of cell electrophysiological sensor chip 4. Thus, convex portion 22 is fitted to concave section 21 of frame substrate 2 and embedded therein. Here, with respect to well 1 and void substrate 3, since the basic structures are not changed, the detailed description thereof is omitted.

With this structure, since fourth opening section 10 of first through hole 5 formed in frame substrate 2 is made to come closer to thin plate 17 of cell electrophysiological sensor chip 4, an exchanging process for medicines, a charging process of cells 19 and the like can be carried out very efficiently from well 1; thus, it becomes possible to provide an efficient measuring process.

With this arrangement, the assembling process of frame substrate 2 and cell electrophysiological sensor chip 4 can be completed by fitting convex portion 22 to concave section 21. Therefore, another advantage in the structure is that upon assembling, no alignment is particularly required.

Moreover, in the same manner as those shown in embodiment 1, all well 1, frame substrate 2 and void substrate 3 are formed by resin, and in particular, these are preferably made from a thermoplastic resin. With this arrangement, these members can be firmly joined to one another by means of thermal fusion or the like, without the necessity of particularly using a bonding agent. Moreover, well 1, frame substrate 2 and void substrate 3 preferably include at least one of polycarbonate resin, polyethylene resin, olefin polymer resin and polymethacrylic acid methylacetate resin. These materials are easily joined, in particular, through thermal fusion. Moreover, each of well 1, frame substrate 2 and void substrate 3 is preferably formed by using at least one material selected from the group consisting of a cyclic olefin polymer, a linear olefin polymer, a cyclic olefin copolymer made by copolymerizing these, and polyethylene. In particular, the cyclic olefin copolymer is superior in transparency and in resistance against alkaline or acidic inorganic medicines, and best suited for manufacturing processes or the application environment of the present invention.

Figure 19:
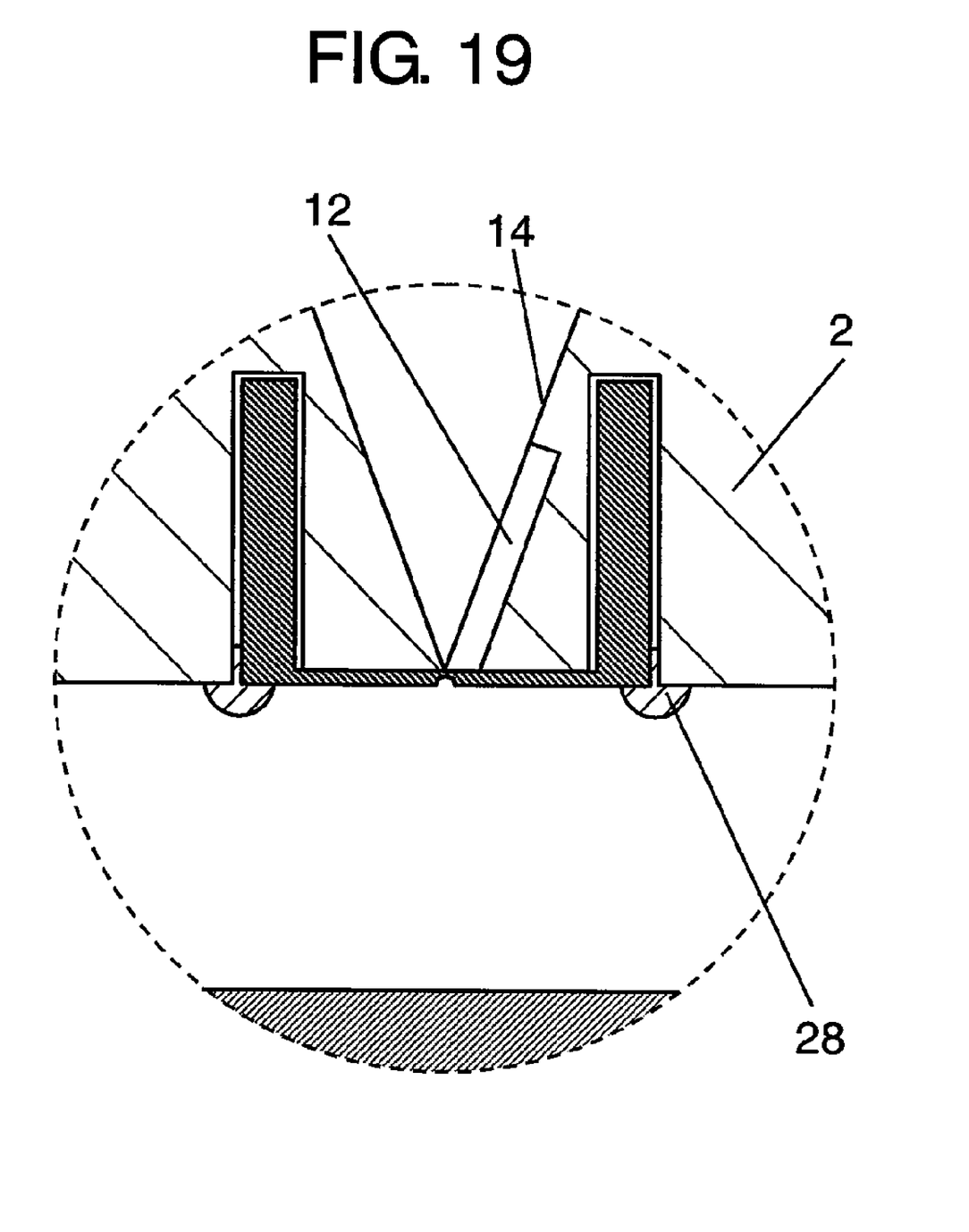
FIG. 19 is a cross-sectional view that shows a chip portion of the cell electrophysiological sensor in accordance with embodiment 2 of the present invention.

Moreover, in the same manner as embodiment 1, as shown in FIG. 19, at least one linear groove 12 is preferably formed radially toward the center of first through hole 5 on second wall 14 that is connected to third opening section 9 of frame substrate 2. With this shape, even in the case when, upon insertion of micropipette 18 from well 1, micropipette 18 is subjected to a stress by the surface tension and the like of the solution in well 1 to cause difficulty in carrying out a positioning process with high precision, by allowing micropipette 18 to come into contact with second wall 14, groove 12 serves as a guide so that cells 19, medicines and the like can be more positively charged to the vicinity of cell electrophysiological sensor chip 4 attached to first through hole 5.

Furthermore, in the same manner as embodiment 1, at least one helical groove 20 may be formed on second wall 14 of frame substrate 2. With this arrangement, the liquid to be charged by micropipette 18 is allowed to flow along helical groove 20; thus, the medicines in the container of well 1 can be easily mixed.

Embodiment 3

Figure 20:
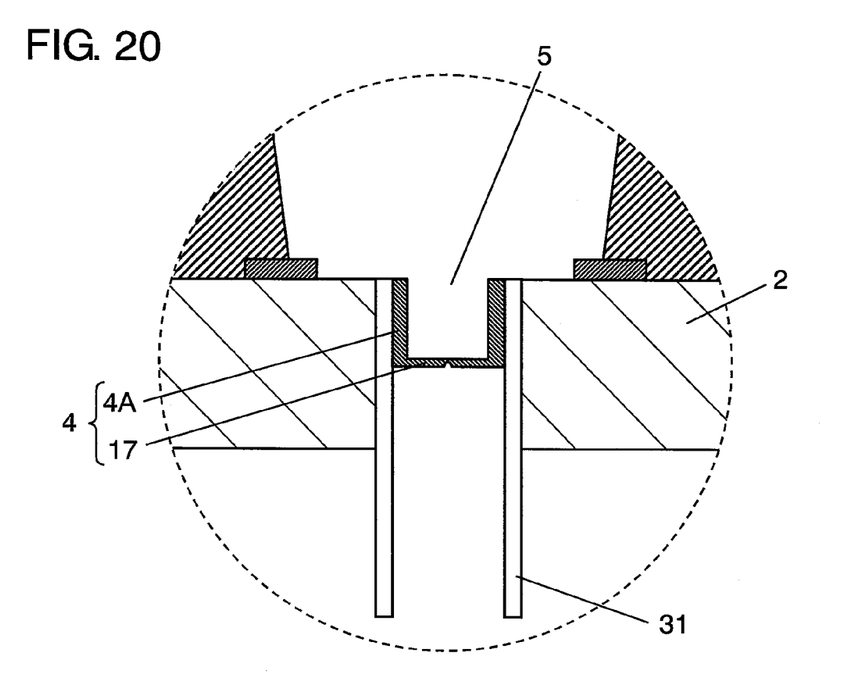
FIG. 20 is an enlarged cross-sectional view that shows a chip portion of a cell electrophysiological sensor in accordance with embodiment 3 of the present invention.

The following description will discuss embodiment 3. FIG. 20 is a cross-sectional view showing a cell electrophysiological sensor in accordance with embodiment 3. As shown in FIG. 20, void structured body 31 is inserted in frame substrate 2 in which first through hole 5 is formed, and cell electrophysiological sensor chip 4 is installed in void structured body 31. In this case, cell electrophysiological sensor chip 4 is placed in such a manner that thin plate 17 is positioned below the opening on the upper side of void structured body 31.

Figure 21:
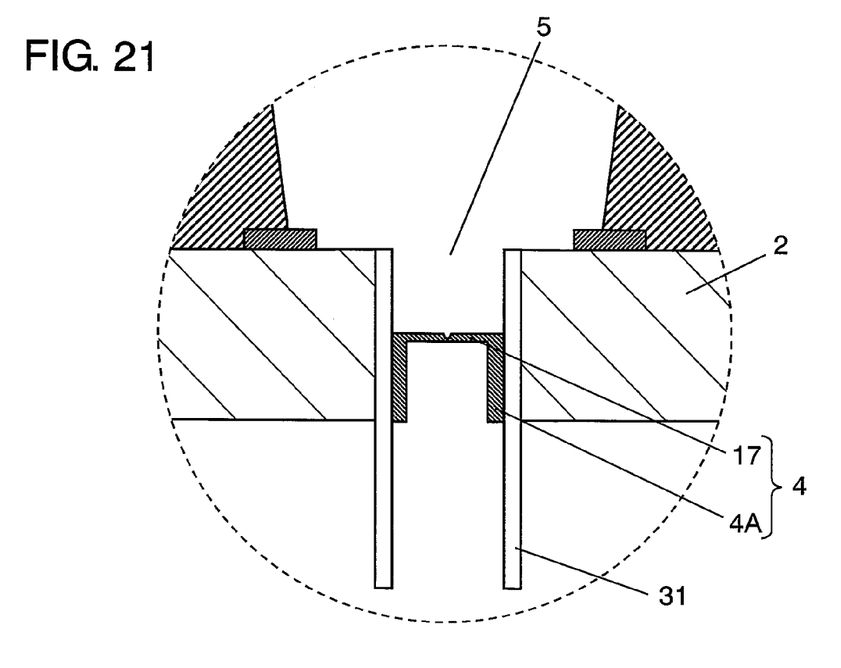
FIG. 21 is an enlarged cross-sectional view that shows a chip portion of a cell electrophysiological sensor in accordance with embodiment 3 of the present invention.

With this arrangement, since thin plate 17 is positioned below the opening on the upper side of void structured body 31, it becomes possible to generate a more moderate flow upon charging medicines and cells from the upper portion, which is the same advantage as that of embodiment 1. Here, as shown in FIG. 21, cell electrophysiological sensor chip 4 may be placed in such a manner as to reverse the positional relationship between holding plate 4A and thin plate 17, and this selection should be made optimally depending on what conditions (flow rate, flow direction, or the like) are used to generate a flow of the cells, medicines and the like to be charged, or depending on the characteristics (for example, floating property, viscosity, size, density, or the like) of the cells to be measured.

INDUSTRIAL APPLICABILITY

As described above, the cell electrophysiological sensor in accordance with the present invention is designed so that, by allowing medicine and other liquids to be positively supplied and sucked to the periphery of a cell that is placed at a specific position in a liquid, measurements can be efficiently carried out on cell electrophysiological phenomena; therefore, the present invention is effectively utilized as measuring apparatuses, such as a medicine screening, that quickly conduct pharmacologic determinations.

The invention claimed is:

1. A cell electrophysiological sensor comprising:
    a well having a first wall formed by at least one curved face, with a first opening section and a second opening section being formed on the two ends of the first wall;
    a frame substrate having a first through hole with a third opening section that is made in contact with the second opening section and a fourth opening section;
    a cell electrophysiological sensor chip that is provided with a thin plate and a side wall portion, said thin plate extending radially inward from the side wall portion and having at least one second through hole, and embedded in the first through hole; and
    a void substrate in which a void is formed so as to be made in contact with the fourth opening section,
    wherein the thin plate of the cell electrophysiological sensor chip is placed below the end portion of the third opening section.

2. The cell electrophysiological sensor according to claim 1, wherein the frame substrate has a thickness greater than a thickness of the cell electrophysiological sensor chip and an opening diameter of the third opening section is made larger than an opening diameter of the fourth opening section.

3. The cell electrophysiological sensor according to claim 1, wherein the well, the frame substrate and the void substrate are made from a thermoplastic resin.

4. The cell electrophysiological sensor according to claim 1, wherein the well, the frame substrate and the void substrate are made from a thermoplastic resin containing at least one of polycarbonate resin, polyethylene resin, olefin polymer resin and polymethacrylic acid methylacetate resin.

5. The cell electrophysiological sensor according to claim 1, wherein the well, the frame substrate and the void substrate are made from at least one material selected from the group consisting of cyclic olefin polymer, linear olefin polymer, cyclic olefin copolymer formed by copolymerizing the two polymers, and polyethylene.

6. The cell electrophysiological sensor according to claim 1, wherein a size of the third opening section is set not larger than a size of the second opening section, and a size of the third opening section is made gradually smaller so as to substantially match a size of a top face of the cell electrophysiological sensor chip by using a taper-shaped second wall.

7. The cell electrophysiological sensor according to claim 6, wherein the taper-shaped second wall of the first through hole is provided with at least one groove toward a center of the first through hole.

8. The cell electrophysiological sensor according to claim 7, wherein the groove is formed in a linear shape.

9. The cell electrophysiological sensor according to claim 7, wherein the groove is formed in a helical shape.

10. The cell electrophysiological sensor according to claim 1, wherein a size of the third opening section is set not larger than size of the second opening section, and the third opening section is prepared as counter bore so as to have substantially the same height up to a height of a top face of the cell electrophysiological sensor chip, with a bottom face forming a plane being formed on the same face as the top face of the cell electrophysiological sensor chip.

11. The cell electrophysiological sensor according to claim 10, wherein at least one linear groove is formed on the bottom face of the third opening section toward a center of the first through hole.

12. The cell electrophysiological sensor according to claim 10, wherein at least one helical groove is formed on the bottom face of the third opening section toward a center of the first through hole.

13. The cell electrophysiological sensor according to claim 10, wherein a star-shaped concave section having a plurality of tip portions is formed on the bottom face of the third opening section.

14. A cell electrophysiological sensor comprising:

a well having a first wall formed by at least one curved face, with a first opening section and a second opening section being formed on the two ends of the first wall;

a frame substrate having a first through hole with a third opening section and a fourth opening section, the third opening section being made in contact with the second opening section;

a void structured body that has a void and is embedded in the first through hole; and a cell electrophysiological sensor chip that is installed in the void of the void structured body, the cell electrophysiological sensor being provided with a thin plate and a side wall portion, the thin plate extending radially inward from the side wall portion, the thin plate having at least one second through hole, wherein the thin plate of the cell electrophysiological sensor chip is placed below the third opening section.

15. A cell electrophysiological sensor comprising:

a well having a first wall formed by at least one curved face, with a first opening section and a second opening section being formed on the two ends of the first wall;

a frame substrate having a first through hole with a third opening section that is made in contact with the second opening section and a fourth opening section, with the third opening section having an opening diameter greater than that of the fourth opening section, with a concave section being formed on a peripheral edge of the fourth opening section;

a cell electrophysiological sensor chip that has a thin plate and a convex portion, the thin plate having at least one second through hole, the cell electrophysiological sensor chip being embedded with the convex portion being fitted to the concave section of the frame substrate, the thin plate extending radially inward from the convex portion; and a void substrate having a void so as to make contact with the fourth opening section, wherein the frame substrate has a thickness that is larger than a thickness of the cell electrophysiological sensor chip.

16. The cell electrophysiological sensor according to claim 15, wherein the well, the frame substrate and the void substrate are made from a thermoplastic resin.

17. The cell electrophysiological sensor according to claim 15, wherein the well, the frame substrate and the void substrate include at least one of polycarbonate resin, polyethylene resin, olefin polymer resin and polymethacrylic acid methylacetate resin.

18. The cell electrophysiological sensor according to claim 15, wherein the well, the frame substrate and the void substrate are made from at least one material selected from the group consisting of cyclic olefin polymer, linear olefin polymer, cyclic olefin copolymer formed by copolymerizing the two polymers, and polyethylene.

19. The cell electrophysiological sensor according to claim 15, wherein a size of the third opening is set not larger than a size of the second opening section, and a size of the third opening section is made gradually smaller so as to substantially match a size of a top face of the cell electrophysiological sensor chip by using a taper-shaped second wall.

20. The cell electrophysiological sensor according to claim 19, wherein the taper-shaped second wall of the first through hole is provided with at least one groove toward the center of the first through hole.

21. The cell electrophysiological sensor according to claim 19, wherein the groove is formed in a linear shape.

22. The cell electrophysiological sensor according to claim 19, wherein the groove is formed in a helical shape.

* * * * *